United States Patent
Kadam

(10) Patent No.: US 11,839,380 B2
(45) Date of Patent: *Dec. 12, 2023

(54) ELECTROLYTIC AND MECHANICAL DETACHMENT FOR IMPLANT DELIVERY SYSTEMS

(71) Applicant: Covidien LP, Mansfield, MA (US)

(72) Inventor: Madhur Kadam, Lake Forest, CA (US)

(73) Assignee: COVIDIEN LP, Mansfield, MA (US)

( * ) Notice: Subject to any disclaimer, the term of this patent is extended or adjusted under 35 U.S.C. 154(b) by 523 days.

This patent is subject to a terminal disclaimer.

(21) Appl. No.: 16/948,570

(22) Filed: Sep. 23, 2020

(65) Prior Publication Data

US 2021/0052277 A1 Feb. 25, 2021

Related U.S. Application Data

(62) Division of application No. 15/784,557, filed on Oct. 16, 2017, now Pat. No. 10,874,401, which is a (Continued)

(51) Int. Cl.
*A61B 17/12* (2006.01)
*A61B 17/00* (2006.01)

(52) U.S. Cl.
CPC .. *A61B 17/12113* (2013.01); *A61B 17/12136* (2013.01); *A61B 17/12145* (2013.01); (Continued)

(58) Field of Classification Search
CPC ........ A61B 17/12113; A61B 17/12136; A61B 17/12145; A61B 17/12172; A61B 2017/00526; A61B 2017/12063
See application file for complete search history.

(56) References Cited

U.S. PATENT DOCUMENTS 1,283,434 A   10/1918   Warren
5,108,407 A    4/1992   Geremia et al.
(Continued)

FOREIGN PATENT DOCUMENTS

DE    4445715 A1   6/1996
EP    0484468 A1   5/1992
(Continued)

OTHER PUBLICATIONS

European Search Report and Opinion dated Mar. 9, 2016; European Application No. 15180213.9; 14 pages.

*Primary Examiner* — Tan-Uyen T Ho
*Assistant Examiner* — Chima U Igboko
(74) *Attorney, Agent, or Firm* — FORTEM IP LLP

(57) ABSTRACT

Detachment of a medical device from a delivery assembly can utilize features of electrolytic detachment and features of mechanical detachment. Detachment zones can facilitate mechanical retention of the medical device as well as electrolytic corrosion of portions of the delivery assembly to allow mechanical release of the medical device. Such a delivery system, can include an implant comprising a hub, the hub defining an aperture having an aperture cross-sectional dimension; and a delivery wire comprising (i) a core member extending through the aperture and (ii) a stopper positioned distal to the aperture, the stopper having a first cross-sectional dimension larger than the aperture cross-sectional dimension, and the stopper being electrolytically corrodible to reduce the first cross-sectional dimension to a second cross-sectional dimension smaller than the aperture cross-sectional dimension.

18 Claims, 6 Drawing Sheets

Related U.S. Application Data division of application No. 14/454,930, filed on Aug. 8, 2014, now Pat. No. 9,814,466.

(52) U.S. Cl.
CPC .................. *A61B 17/12172* (2013.01); *A61B 2017/00526* (2013.01); *A61B 2017/12063* (2013.01)

(56) References Cited

U.S. PATENT DOCUMENTS

| | | | |
|---|---|---|---|
| 5,122,136 A | 6/1992 | Guglielmi et al. | |
| 5,250,071 A | 10/1993 | Palermo | |
| 5,354,295 A | 10/1994 | Guglielmi et al. | |
| 5,370,653 A | 12/1994 | Cragg | |
| 5,423,829 A | 6/1995 | Pham et al. | |
| 5,522,836 A | 6/1996 | Palermo | |
| 5,540,680 A | 7/1996 | Guglielmi et al. | |
| 5,624,449 A | 4/1997 | Pham et al. | |
| 5,658,308 A | 8/1997 | Snyder | |
| 5,669,931 A | 9/1997 | Kupiecki et al. | |
| 5,690,667 A | 11/1997 | Gia | |
| 5,733,329 A | 3/1998 | Wallace et al. | |
| 5,743,905 A | 4/1998 | Eder et al. | |
| 5,749,894 A | 5/1998 | Engelson | |
| 5,766,629 A | 6/1998 | Cho et al. | |
| 5,800,455 A | 9/1998 | Palermo et al. | |
| 5,851,206 A | 12/1998 | Guglielmi et al. | |
| 5,853,418 A | 12/1998 | Ken et al. | |
| 5,855,578 A | 1/1999 | Guglielmi et al. | |
| 5,891,128 A | 4/1999 | Gia et al. | |
| 5,895,385 A | 4/1999 | Guglielmi et al. | |
| 5,916,235 A | 6/1999 | Guglielmi | |
| 5,919,187 A | 7/1999 | Guglielmi et al. | |
| 5,925,037 A | 7/1999 | Guglielmi et al. | |
| 5,925,059 A | 7/1999 | Palermo et al. | |
| 5,928,226 A | 7/1999 | Guglielmi et al. | |
| 5,935,145 A | 8/1999 | Villar et al. | |
| 5,941,888 A | 8/1999 | Wallace et al. | |
| 5,944,714 A | 8/1999 | Guglielmi et al. | |
| 5,947,962 A | 9/1999 | Guglielmi et al. | |
| 5,947,963 A | 9/1999 | Guglielmi | |
| 5,951,599 A | 9/1999 | Mccrory | |
| 5,964,797 A | 10/1999 | Ho | |
| 5,976,126 A | 11/1999 | Guglielmi | |
| 5,984,929 A | 11/1999 | Bashiri et al. | |
| 6,010,498 A | 1/2000 | Guglielmi | |
| 6,013,084 A | 1/2000 | Ken et al. | |
| 6,059,779 A | 5/2000 | Mills | |
| 6,063,070 A | 5/2000 | Eder | |
| 6,063,104 A | 5/2000 | Villar et al. | |
| 6,066,133 A | 5/2000 | Guglielmi et al. | |
| 6,077,260 A | 6/2000 | Wheelock et al. | |
| 6,083,220 A | 7/2000 | Guglielmi et al. | |
| 6,123,714 A | 9/2000 | Gia et al. | |
| 6,136,015 A | 10/2000 | Kurz et al. | |
| 6,146,373 A | 11/2000 | Cragg et al. | |
| 6,156,061 A | 12/2000 | Wallace et al. | |
| 6,165,178 A | 12/2000 | Bashiri et al. | |
| 6,168,592 B1 | 1/2001 | Kupiecki et al. | |
| 6,168,615 B1 | 1/2001 | Ken et al. | |
| 6,168,618 B1 | 1/2001 | Frantzen | |
| 6,193,728 B1 | 2/2001 | Ken et al. | |
| 6,238,403 B1 | 5/2001 | Greene et al. | |
| 6,241,691 B1 | 6/2001 | Ferrera et al. | |
| 6,280,457 B1 | 8/2001 | Wallace et al. | |
| 6,296,622 B1 | 10/2001 | Kurz et al. | |
| 6,299,619 B1 | 10/2001 | Greene et al. | |
| 6,306,153 B1 | 10/2001 | Kurz et al. | |
| 6,309,367 B1 | 10/2001 | Boock | |
| 6,371,972 B1 | 4/2002 | Wallace et al. | |
| 6,409,721 B1 | 6/2002 | Wheelock et al. | |
| 6,416,373 B1 | 7/2002 | Kolb et al. | |
| 6,425,893 B1 | 7/2002 | Guglielmi | |
| 6,425,914 B1 | 7/2002 | Wallace et al. | |
| 6,468,266 B1 | 10/2002 | Bashiri et al. | |
| 6,468,301 B1 | 10/2002 | Amplatz et al. | |
| 6,478,773 B1 | 11/2002 | Gandhi et al. | |
| 6,485,524 B2 | 11/2002 | Strecker | |
| 6,486,266 B2 | 11/2002 | Amano et al. | |
| 6,511,468 B1 | 1/2003 | Cragg et al. | |
| 6,533,801 B2 | 3/2003 | Wallace et al. | |
| 6,558,367 B1 | 5/2003 | Cragg et al. | |
| 6,589,230 B2 | 7/2003 | Gia et al. | |
| 6,589,236 B2 | 7/2003 | Wheelock et al. | |
| 6,591,472 B1 | 7/2003 | Noone et al. | |
| 6,602,261 B2 | 8/2003 | Greene et al. | |
| 6,605,101 B1 | 8/2003 | Schaefer et al. | |
| 6,620,152 B2 | 9/2003 | Guglielmi | |
| 6,623,493 B2 | 9/2003 | Wallace et al. | |
| 6,723,112 B2 | 4/2004 | Ho et al. | |
| 6,743,251 B1 | 6/2004 | Eder | |
| 6,835,185 B2 | 12/2004 | Ramzipoor et al. | |
| 6,878,384 B2 | 4/2005 | Cruise et al. | |
| 6,905,503 B2 * | 6/2005 | Gifford, III | A61B 17/1214 606/151 |
| 6,936,055 B1 | 8/2005 | Ken et al. | |
| 6,953,473 B2 | 10/2005 | Porter | |
| 6,964,657 B2 | 11/2005 | Cragg et al. | |
| 6,966,892 B2 | 11/2005 | Gandhi et al. | |
| 7,014,645 B2 | 3/2006 | Greene et al. | |
| 7,083,567 B2 | 8/2006 | Mawad | |
| 7,128,736 B1 | 10/2006 | Abrams et al. | |
| 7,166,122 B2 | 1/2007 | Aganon et al. | |
| 7,169,172 B2 | 1/2007 | Levine et al. | |
| 7,198,613 B2 | 4/2007 | Gandhi et al. | |
| 7,229,461 B2 | 6/2007 | Chin et al. | |
| 7,238,194 B2 | 7/2007 | Monstadt et al. | |
| 7,255,707 B2 | 8/2007 | Ramzipoor et al. | |
| 7,300,458 B2 | 11/2007 | Henkes et al. | |
| 7,323,000 B2 | 1/2008 | Monstdt et al. | |
| 7,331,974 B2 | 2/2008 | Schaefer et al. | |
| 7,485,122 B2 | 2/2009 | Teoh | |
| 7,524,322 B2 | 4/2009 | Monstadt et al. | |
| 7,601,160 B2 | 10/2009 | Richter | |
| 7,608,089 B2 | 10/2009 | Wallace et al. | |
| RE41,029 E | 12/2009 | Guglielmi et al. | |
| 7,651,513 B2 | 1/2010 | Teoh et al. | |
| 7,695,484 B2 | 4/2010 | Wallace et al. | |
| 7,879,064 B2 | 2/2011 | Monstadt et al. | |
| 7,896,899 B2 | 3/2011 | Patterson et al. | |
| 7,938,845 B2 | 5/2011 | Aganon et al. | |
| RE42,625 E | 8/2011 | Guglielmi | |
| 8,002,789 B2 | 8/2011 | Ramzipoor et al. | |
| RE42,756 E | 9/2011 | Guglielmi et al. | |
| 8,016,869 B2 * | 9/2011 | Nikolchev | A61B 17/12136 623/1.11 |
| 8,021,416 B2 | 9/2011 | Abrams | |
| 8,043,326 B2 | 10/2011 | Hancock et al. | |
| 8,048,104 B2 | 11/2011 | Monstadt et al. | |
| RE43,311 E | 4/2012 | Wallace et al. | |
| 8,157,855 B2 | 4/2012 | Eidenschink et al. | |
| 8,202,292 B2 | 6/2012 | Kellett | |
| 8,221,396 B2 | 7/2012 | Dehnad et al. | |
| 8,221,483 B2 | 7/2012 | Ford et al. | |
| 8,273,116 B2 | 9/2012 | Licata et al. | |
| 8,298,256 B2 | 10/2012 | Gandhi et al. | |
| 8,328,860 B2 | 12/2012 | Strauss et al. | |
| 8,372,110 B2 | 2/2013 | Monstadt et al. | |
| 8,398,671 B2 | 3/2013 | Chen et al. | |
| 8,425,541 B2 | 4/2013 | Masters et al. | |
| 8,470,013 B2 | 6/2013 | Duggal et al. | |
| 8,480,701 B2 | 7/2013 | Monstadt | |
| 8,562,667 B2 | 10/2013 | Cox | |
| 8,597,321 B2 | 12/2013 | Monstadt et al. | |
| 8,632,584 B2 | 1/2014 | Henkes et al. | |
| 8,641,746 B2 | 2/2014 | Andreas et al. | |
| 8,641,777 B2 | 2/2014 | Strauss et al. | |
| 8,652,163 B2 | 2/2014 | Padilla et al. | |
| 8,657,870 B2 | 2/2014 | Turovskiy et al. | |
| 8,715,312 B2 | 5/2014 | Burke et al. | |
| 8,715,317 B1 | 5/2014 | Janardhan et al. | |
| 8,721,625 B2 | 5/2014 | Klint | |
| 8,728,142 B2 | 5/2014 | Gandhi et al. | |

(56) References Cited

U.S. PATENT DOCUMENTS

| | | |
|---|---|---|
| 8,777,978 B2 | 7/2014 | Strauss et al. |
| 8,777,979 B2 | 7/2014 | Shrivastava et al. |
| 8,795,320 B2 | 8/2014 | Strauss et al. |
| 8,795,321 B2 | 8/2014 | Strauss et al. |
| 8,801,747 B2 | 8/2014 | Strauss et al. |
| 8,845,676 B2 | 9/2014 | Monstadt et al. |
| 8,864,790 B2 | 10/2014 | Strauss et al. |
| 8,870,909 B2 | 10/2014 | Cox |
| 8,876,863 B2 | 11/2014 | Eskridge |
| 8,900,285 B2 | 12/2014 | Licata |
| 8,906,057 B2 | 12/2014 | Connor et al. |
| 8,915,950 B2 | 12/2014 | Cam et al. |
| 8,926,681 B2 | 1/2015 | Levy et al. |
| 8,932,317 B2 | 1/2015 | Marks et al. |
| 8,940,011 B2 | 1/2015 | Teoh et al. |
| 8,974,509 B2 | 3/2015 | Licata |
| 8,974,513 B2 | 3/2015 | Ford et al. |
| 8,992,563 B2 | 3/2015 | Chen |
| 8,998,926 B2 | 4/2015 | Pomeranz |
| 9,039,749 B2 | 5/2015 | Shrivastava et al. |
| 9,050,095 B2 | 6/2015 | Monstadt et al. |
| 9,055,948 B2 | 6/2015 | Jaeger et al. |
| 9,211,202 B2 | 12/2015 | Strother et al. |
| 9,486,224 B2 | 11/2016 | Riina et al. |
| 9,814,466 B2 | 11/2017 | Kadam |
| 9,833,309 B2 | 12/2017 | Levi et al. |
| 9,844,380 B2 | 12/2017 | Furey |
| 9,907,684 B2 | 3/2018 | Connor et al. |
| 9,962,146 B2 | 5/2018 | Hebert et al. |
| 10,028,745 B2 | 7/2018 | Morsi |
| 2001/0000797 A1 | 5/2001 | Mazzocchi |
| 2001/0001835 A1 | 5/2001 | Greene et al. |
| 2002/0151883 A1 | 10/2002 | Guglielmi |
| 2003/0014073 A1 | 1/2003 | Bashiri et al. |
| 2003/0018294 A1 | 1/2003 | Cox |
| 2003/0028209 A1 | 2/2003 | Teoh et al. |
| 2003/0040733 A1 | 2/2003 | Cragg et al. |
| 2003/0040772 A1 | 2/2003 | Hyodoh et al. |
| 2003/0176857 A1 | 9/2003 | Lee |
| 2003/0225365 A1 | 12/2003 | Greff et al. |
| 2004/0002731 A1 | 1/2004 | Aganon et al. |
| 2004/0225279 A1 | 11/2004 | Raymond |
| 2004/0236344 A1 | 11/2004 | Monstadt et al. |
| 2005/0079196 A1 | 4/2005 | Henkes et al. |
| 2005/0267511 A1 | 12/2005 | Marks et al. |
| 2006/0036281 A1 | 2/2006 | Patterson et al. |
| 2006/0135986 A1 | 6/2006 | Wallace et al. |
| 2006/0155323 A1 | 7/2006 | Porter et al. |
| 2006/0200234 A1 | 9/2006 | Hines |
| 2006/0206199 A1 | 9/2006 | Churchwell et al. |
| 2006/0271097 A1 | 11/2006 | Ramzipoor et al. |
| 2007/0014831 A1 | 1/2007 | Sung et al. |
| 2007/0073334 A1* | 3/2007 | Ramzipoor ...... A61B 17/12145 606/200 |
| 2007/0100426 A1 | 5/2007 | Rudakov et al. |
| 2007/0175536 A1 | 8/2007 | Monetti et al. |
| 2007/0191924 A1 | 8/2007 | Rudakov |
| 2008/0045922 A1 | 2/2008 | Cragg et al. |
| 2008/0051803 A1 | 2/2008 | Monjtadt et al. |
| 2008/0103585 A1 | 5/2008 | Monstadt et al. |
| 2008/0125855 A1 | 5/2008 | Henkes et al. |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0143786 A1 | 6/2009 | Bashiri et al. |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0144895 A1 | 6/2010 | Porter |
| 2010/0256666 A1 | 10/2010 | Chen et al. |
| 2010/0331948 A1 | 12/2010 | Turovskiy et al. |
| 2011/0098814 A1 | 4/2011 | Monstadt et al. |
| 2011/0106128 A1 | 5/2011 | Chen |
| 2011/0118768 A1 | 5/2011 | Tran et al. |
| 2011/0118777 A1 | 5/2011 | Patterson et al. |
| 2011/0137405 A1 | 6/2011 | Wilson et al. |
| 2011/0184453 A1 | 7/2011 | Levy et al. |
| 2012/0010648 A1 | 1/2012 | Monstadt et al. |
| 2012/0209310 A1 | 8/2012 | Chen et al. |
| 2012/0271344 A1 | 10/2012 | Ford et al. |
| 2012/0316632 A1 | 12/2012 | Gao |
| 2013/0138198 A1 | 5/2013 | Aporta et al. |
| 2013/0184743 A1 | 7/2013 | Chen et al. |
| 2013/0211492 A1 | 8/2013 | Schneider et al. |
| 2013/0274866 A1 | 10/2013 | Cox et al. |
| 2014/0005651 A1 | 1/2014 | Eskridge |
| 2014/0012307 A1 | 1/2014 | Franano et al. |
| 2014/0039535 A1 | 2/2014 | Eskuri |
| 2014/0058420 A1 | 2/2014 | Hannes et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0135818 A1 | 5/2014 | Gandhi et al. |
| 2014/0142608 A1 | 5/2014 | Eskridge et al. |
| 2014/0148843 A1 | 5/2014 | Strauss et al. |
| 2014/0163604 A1 | 6/2014 | Monstadt |
| 2014/0236217 A1 | 8/2014 | Gandhi et al. |
| 2014/0277092 A1 | 9/2014 | Teoh et al. |
| 2014/0277094 A1 | 9/2014 | Chen et al. |
| 2014/0288633 A1 | 9/2014 | Burke et al. |
| 2014/0316012 A1 | 10/2014 | Freyman et al. |
| 2014/0371734 A1 | 12/2014 | Truckai |
| 2014/0371839 A1 | 12/2014 | Henkes et al. |
| 2015/0005804 A1 | 1/2015 | Franano et al. |
| 2015/0057700 A1 | 2/2015 | Chen et al. |
| 2015/0066073 A1 | 3/2015 | Ma |
| 2015/0105817 A1 | 4/2015 | Marchand et al. |
| 2015/0133990 A1 | 5/2015 | Davidson |
| 2015/0142042 A1 | 5/2015 | Cox |
| 2015/0150563 A1 | 6/2015 | Marchand et al. |
| 2015/0157331 A1 | 6/2015 | Levy et al. |
| 2015/0164665 A1 | 6/2015 | Cam et al. |
| 2015/0173771 A1 | 6/2015 | Marks et al. |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0022445 A1 | 1/2016 | Ruvalcaba et al. |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |
| 2020/0061099 A1 | 2/2020 | Li et al. |

FOREIGN PATENT DOCUMENTS

| | | |
|---|---|---|
| EP | 0719522 A1 | 7/1996 |
| EP | 0726745 A1 | 8/1996 |
| EP | 0739606 A1 | 10/1996 |
| EP | 0803230 A2 | 10/1997 |
| EP | 0807410 A2 | 11/1997 |
| EP | 0861634 A2 | 9/1998 |
| EP | 1005837 A2 | 6/2000 |
| EP | 1009295 A1 | 6/2000 |
| EP | 1227760 A1 | 8/2002 |
| EP | 1329196 A1 | 7/2003 |

(56) References Cited

FOREIGN PATENT DOCUMENTS

| | | | |
|---|---|---|---|
| EP | 1420701 | A1 | 5/2004 |
| EP | 1843710 | A1 | 10/2007 |
| EP | 1884208 | A1 | 2/2008 |
| EP | 1951129 | A2 | 8/2008 |
| EP | 2124763 | A2 | 12/2009 |
| EP | 2146651 | A2 | 1/2010 |
| EP | 2227163 | A1 | 9/2010 |
| EP | 2334242 | A1 | 6/2011 |
| EP | 2415424 | A2 | 2/2012 |
| EP | 2575697 | A1 | 4/2013 |
| EP | 2668914 | A1 | 12/2013 |
| EP | 2781196 | A2 | 9/2014 |
| EP | 2859854 | A1 | 4/2015 |
| JP | 2005500121 | A | 1/2005 |
| WO | 9113592 | A1 | 9/1991 |
| WO | 9905977 | A1 | 2/1999 |
| WO | 9909894 | A1 | 3/1999 |
| WO | 03011151 | A1 | 2/2003 |
| WO | 2011066962 | A1 | 6/2011 |
| WO | 2012166804 | A1 | 12/2012 |
| WO | 2013119332 | A2 | 8/2013 |
| WO | 2017074411 | A1 | 5/2017 |
| WO | 2018051187 | A1 | 3/2018 |

* cited by examiner

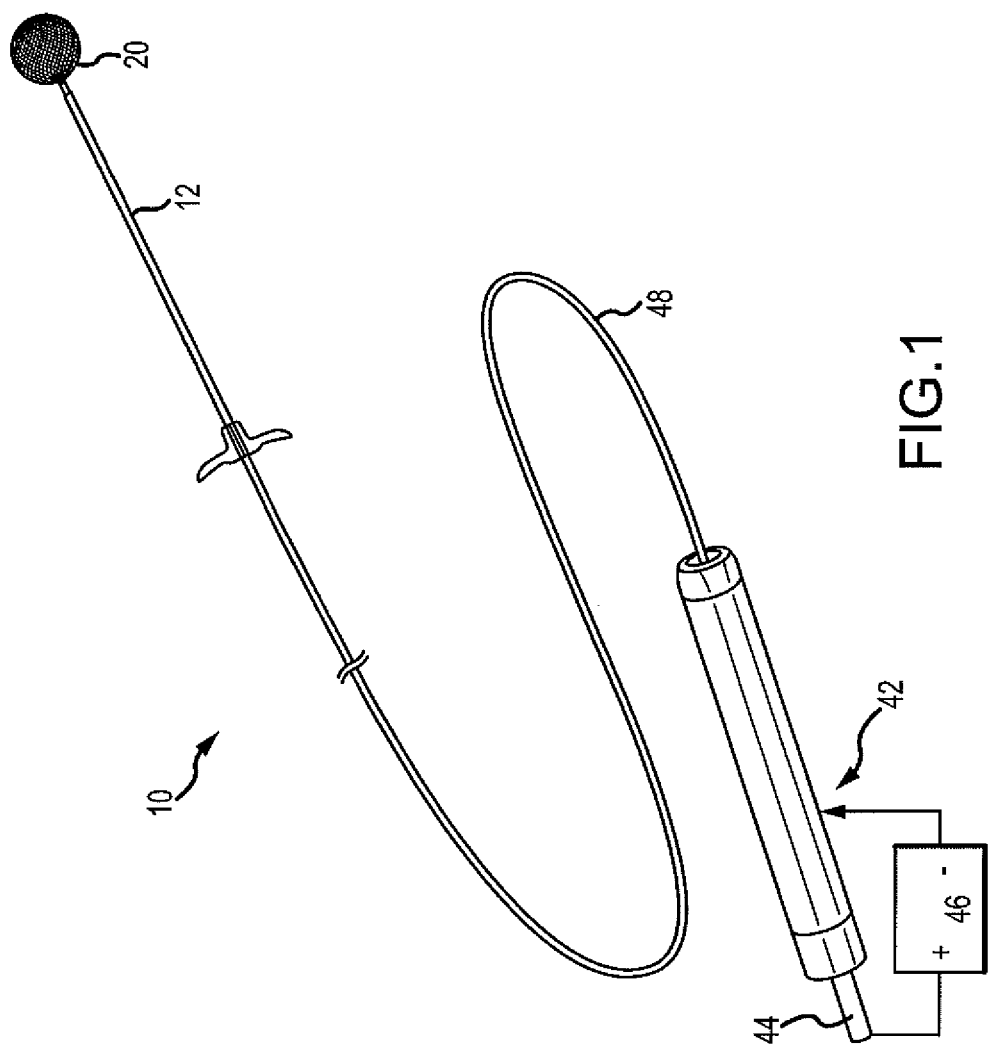

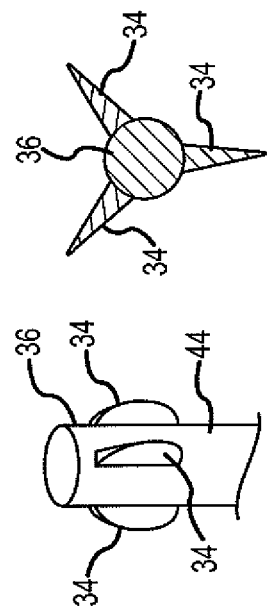
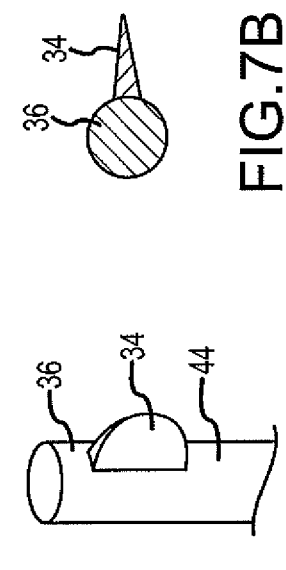
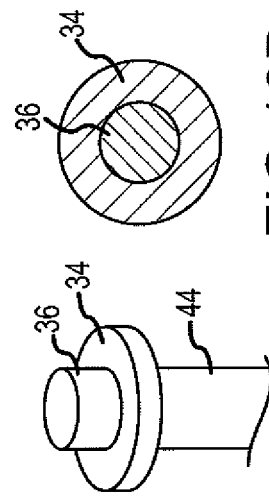
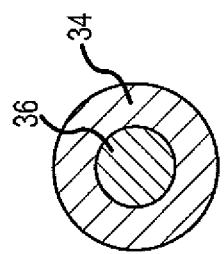

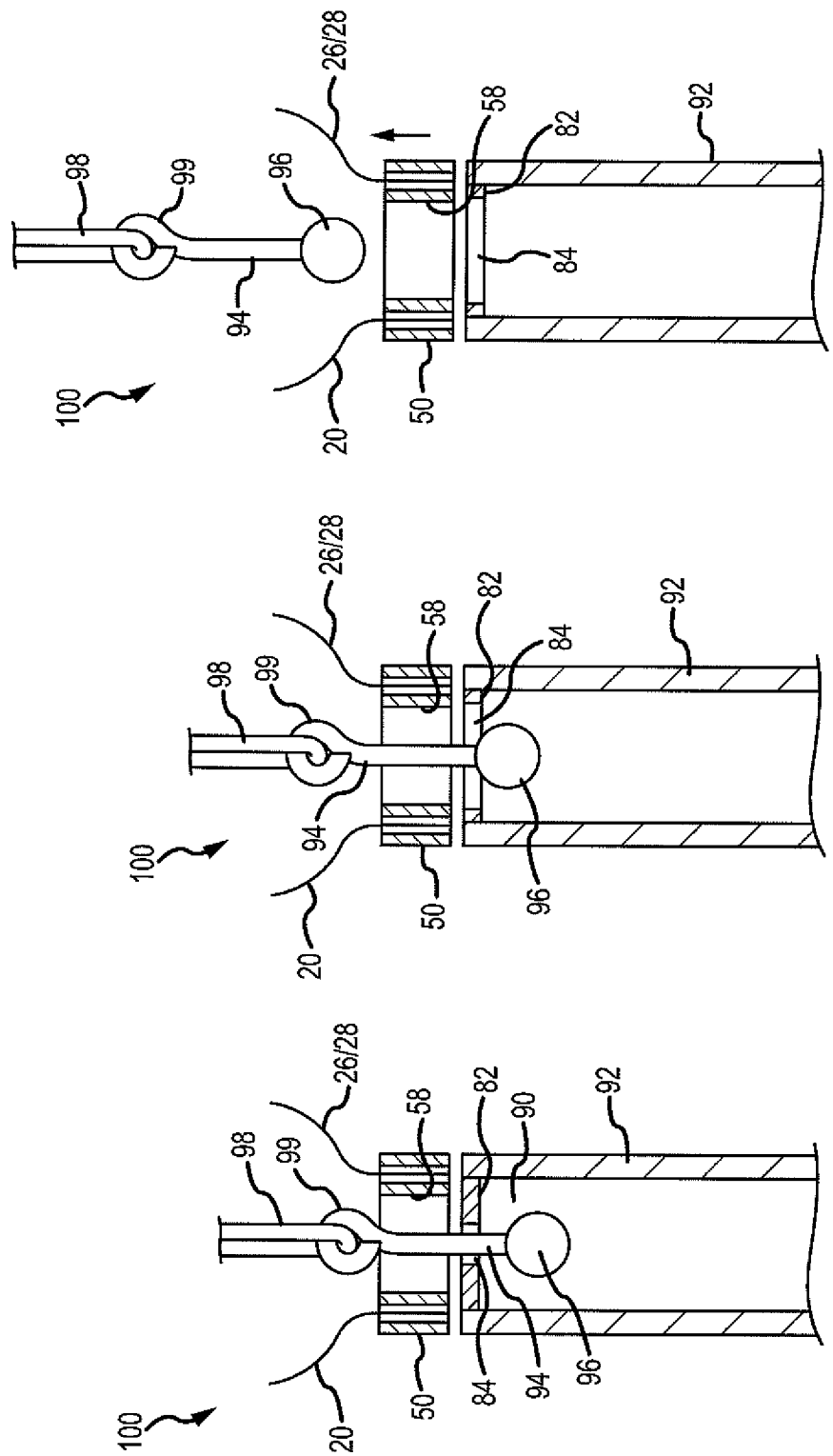

ELECTROLYTIC AND MECHANICAL DETACHMENT FOR IMPLANT DELIVERY SYSTEMS

RELATED APPLICATIONS

This application is a divisional of U.S. patent application Ser. No. 15/784,557, filed Oct. 16, 2017, which is a divisional of U.S. patent application Ser. No. 14/454,930, filed Aug. 8, 2014, now U.S. Pat. No. 9,814,466, both of which are hereby incorporated by reference in their entirety.

FIELD

The subject technology relates to delivery of implantable devices by a delivery system.

BACKGROUND

The use of endovascular techniques for the implantation of medical devices and the occlusion of body cavities such as arteries, veins, fallopian tubes or vascular deformities is known in the art. For example, occlusion of vascular aneurysms can be performed using an implantable device, such as an intrasaccular implant, that is introduced with the aid of an endovascular delivery wire through a catheter. Once moved to the treatment site, the intrasaccular implant can be moved into the aneurysm cavity to occlude the aneurysm.

The severance of the intrasaccular implant from the endovascular delivery wire can be particularly problematic. On the one hand, the device must be as small as possible to be guided through the fine bore of the catheter to its destination, while on the other hand it must bring about a reliable severance of the intrasaccular implant. Absent a reliable severance of the intrasaccular implant, withdrawal of the delivery wire and catheter may cause unintended removal of the intrasaccular implant from the cavity to be occluded and thus injure and/or rupture of the wall of the cavity or vessel.

Traditional mechanical methods for the severance of intrasaccular implants from the insertion means do not take much time to perform. However, the necessary rigidity of the technical features of the connection between the intrasaccular implant and the introduction means can impede the introduction of the implant. Furthermore, the low load carrying capacity of the connection due to its rigidity entails an appreciable risk of premature detachment of the insertion means from the occluding implant. Moreover, in the case of mechanical separation of the inserting wire and the intrasaccular implant, energy must be transmitted (e.g., by rotation of the inserting wire), which may cause the implant to be dislodged out of the correct position.

Traditional electrolytic severance of the intrasaccular implant involves using an electrolytically corrodible design on the end of the delivery wire at the connection between the delivery wire and the intrasaccular implant. Such a device can elegantly makes use of the voltage applied to the intrasaccular implant serving as an anode for electro-thrombization. However, the connection of the implant to the delivery wire is limited by the requirements of the electrolytically corrodible region. For example, the only materials that can be utilized are those which have a sufficiently high degree of strength to enable reliable guidance of the occluding wire through the delivery wire. The selection of materials for forming the point of eventual electrolytic severance is consequently extremely limited. Furthermore, a portion of the implant's connection to the delivery wire may remain protruding from the implant after detachment, presenting a risk of harm to the surrounding anatomy.

In the case of traditional devices for the electrolytic severance of intrasaccular implants, the intrasaccular implant and the delivery wire are not produced integrally, but instead are produced mechanically connected with each other. This design has the inherent disadvantage that the delivery wire must be tapered toward its end in an involved grinding operation in order to ensure sufficient strength in the proximal zone of the delivery wire and to facilitate electrolytic, corrosive severance of the wire end in the distal part of the delivery wire. In order to ensure sufficient strength of the connection point, the corrodible zone of the end of the delivery wire must not have a diameter below a certain minimum value since it is subjected to a high flexural load. The corrodible wire end representing the connection point between the intrasaccular implant and the delivery wire can be consequently extremely rigid and require a relatively long time for electrolytic corrosive severance.

SUMMARY

Electrolytic severance of the implantable medical devices can involve using an electrolytically corrodible design on the end of a delivery wire at the connection between the delivery wire and the medical device. Such a device can elegantly makes use of the voltage applied to the intrasaccular implant serving as an anode for electro-thrombization.

At least one aspect of the disclosure provides methods and apparatuses for enabling mechanical detachment of a device or devices (e.g., occluding devices, coils, or stents) following electrolytic corrosion of a mechanical hub between a delivery wire and the device.

According to some embodiments, a delivery system can include an implant comprising a hub, the hub defining an aperture having an aperture cross-sectional dimension; and a delivery wire comprising (i) a core member extending through the aperture and (ii) a stopper positioned distal to the aperture, the stopper having a first cross-sectional dimension that is larger than the aperture cross-sectional dimension, and the stopper being electrolytically corrodible to reduce the first cross-sectional dimension to a second cross-sectional dimension that is smaller than the aperture cross-sectional dimension.

The first cross-sectional dimension can prevent movement of the stopper proximally past the aperture, and the second cross-sectional dimension allows movement of the stopper proximally past the aperture. The core member can be formed of a first material and the stopper can be formed of a second material that is more susceptible to electrolytic corrosion than the first material. The stopper can also include a flange extending radially outwardly from the core member. The flange can have a maximum radial dimension that is smaller than a core member cross-sectional dimension of the core member.

The delivery wire can also include an insulating layer covering a proximal portion of the core member that is at least partially within the aperture. The delivery wire can also include a pusher fixed to the core member at a location proximal to the hub, and having a pusher cross-sectional dimension that is larger than the aperture cross-sectional dimension. The delivery system can also include an electrical power source connected to the delivery wire. The stopper has a maximum cross-sectional area that is smaller than an aperture cross-sectional area of the aperture. At least a portion of the stopper is substantially flat.

According to some embodiments, a method of delivering a vascular implant can include: delivering an implant to a target location while (i) a core member of a delivery wire extends through an aperture defined by a hub of the implant and (ii) a stopper of the delivery wire is positioned distal to the aperture and prevents release of the implant from the delivery wire by a first cross-sectional dimension of the stopper, the first cross-sectional dimension being greater than an aperture cross-sectional dimension; electrolytically corroding the stopper to reduce the first cross-sectional dimension to a second cross-sectional dimension that is smaller than the aperture cross-sectional dimension; and releasing the 'implant from the delivery wire by moving the delivery wire entirely proximally past the aperture.

Delivering the implant can include engaging the hub of the implant with a pusher fixed to the core member at a location proximal to the hub. Delivering the implant can include advancing the implant out of a catheter and into a body lumen of a patient. Electrolytically corroding the stopper can include inducing an electrical current through the core member and the stopper.

According to some embodiments, a method of making a delivery system can include: providing an implant, the implant comprising a hub, the hub defining an aperture having an aperture cross-sectional dimension; and providing a delivery wire to the implant such that (i) a core member of the delivery wire extends through the aperture and (ii) a stopper of the delivery wire is positioned distal to the aperture, the stopper having a first cross-sectional dimension that is larger than the aperture cross-sectional dimension, and the stopper being electrolytically corrodible to reduce the first cross-sectional dimension to a second cross-sectional dimension that is smaller than the aperture cross-sectional dimension.

Providing the delivery wire can include: distally advancing the core member through the aperture such that a distal end portion of the delivery wire is positioned distal to the aperture; after advancing the core member through the aperture, forming the stopper at the distal end portion. Providing the delivery wire cart include: forming the stopper at a distal end portion of the delivery wire. After forming the stopper, the core member can be proximally advanced through the aperture such that the distal end portion is positioned distal to the aperture. Providing the delivery wire can include stamping a distal end portion of the delivery wire to form the first cross-sectional dimension. Providing the delivery wire can include attaching the stopper to the distal end portion.

According to some embodiments, a delivery system can include a pusher sleeve having an end cap defining an aperture having a first aperture cross-sectional dimension in an engagement state and a second aperture cross-sectional dimension in a corroded state; and an implant comprising an engagement portion (e.g., ball, rod, stretch-resistant member, etc.), at least partially within a cavity distal to the aperture; wherein the engagement portion has an engagement portion cross-sectional dimension that is larger than the first aperture cross-sectional dimension and smaller than the second aperture cross-sectional dimension.

According to some embodiments, a method of delivering a vascular implant can include: delivering an implant to a target location while (i) an engagement portion of the implant extends through an aperture defined by an end cap of a pusher sleeve and (ii) the aperture has a first aperture cross-sectional dimension smaller than an engagement portion cross-sectional dimension; electrolytically corroding the end cap to enlarge the first cross-sectional dimension to a second cross-sectional dimension that is larger than the engagement portion cross-sectional dimension; and releasing the implant from the pusher sleeve.

According to some embodiments, a method of making a delivery system can include: providing an implant, the implant comprising an engagement portion, the end cap defining an aperture having a first aperture cross-sectional dimension smaller than an engagement portion cross-sectional dimension; and providing the engagement portion within a cavity of the pusher sleeve, such that the engagement portion extends through the aperture, wherein the end cap is electrolytically corrodible to enlarge the first cross-sectional dimension to a second cross-sectional dimension that is larger than the engagement portion cross-sectional dimension.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 1 shows a perspective view providing an overview of a treatment system, in accordance with one or more embodiments of the present disclosure.

FIG. 7A shows a perspective view of a distal end of a delivery system, and FIG. 7B shows a sectional view of the distal end of the delivery system, in accordance with one or more embodiments of the present disclosure.

FIG. 8A shows a perspective view of a distal end of a delivery system, and FIG. 8B shows a sectional view of the distal end of the delivery system, in accordance with one or more embodiments of the present disclosure.

FIG. 9A shows a perspective view of a distal end of a delivery system, and FIG. 9B shows a sectional view of the distal end of the delivery system, in accordance with one or more embodiments of the present disclosure.

FIG. 10A shows a perspective view of a distal end of a delivery system, and FIG. 10B shows a sectional view of the distal end of the delivery system, in accordance with one or more embodiments of the present disclosure.

FIGS. 11A, 11B, and 11C, show sectional views of implant detachment with a system, in accordance with one or more embodiments of the present disclosure.

DETAILED DESCRIPTION

Figure 3:
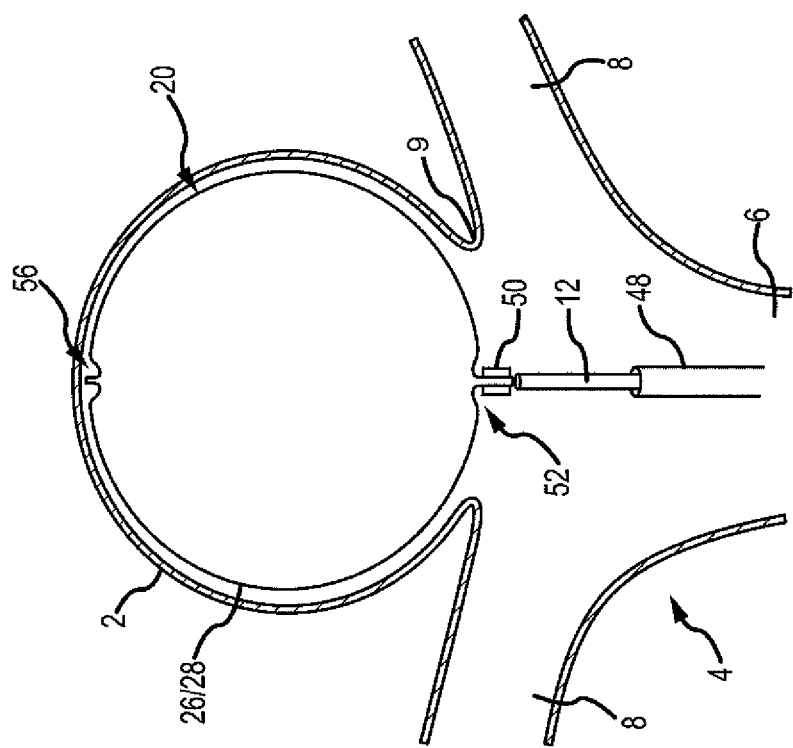
FIG. 3 shows a side-sectional view of a braid ball implant deployed within a bifurcation aneurysm, in accordance with one or more embodiments of the present disclosure.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

In accordance with some embodiments disclosed herein is the realization that detachment of a medical device from a delivery assembly can be improved by utilizing features of electrolytic detachment and features of mechanical detachment. Thus, various embodiments provide for detachment zones that can facilitate electrolytic detachment of a delivery mechanism and mechanical release of the medical device, making the detachment process faster and more reliable.

The medical device can be implanted in body cavities or blood vessels. In addition to the medical device, the delivery system can comprise a voltage source, a cathode, and a catheter. The medical device can be slid in the catheter in the longitudinal direction. A delivery wire may engage the medical device and be adapted to serve as an anode, such that a portion of the delivery wire is designed to be electrolytically corroded at one or more points so that while in contact with a body fluid, one or more portions of the medical device may be released from the delivery wire.

According to some embodiments, FIG. 1 presents an overview of a treatment system IO including an implant 20 and a handle 42. The handle 42 shown provides proximal access to a delivery wire that engages the implant 20 at a distal end. The catheter/pusher shaft 12 can include a simple extrusion (e.g., PTFE, PEP, PEEK, etc.) or can be constructed using conventional catheter construction techniques and include a liner, braid support and outer jacket (not shown). A loading sheath 48 is typically provided over the shaft of a pusher 12.

A power supply 46 may be coupled to a proximal portion of the delivery wire 44. The power supply 46 may also be coupled to a proximal portion of the handle 42 or to the patient. A current can flow from the power supply 46, to a detachment zone at or near the implant 20, and to a return path via the catheter shaft 12 (and/or another structure extending near the detachment zone. Alternatively, the current from the detachment zone may flow to the patient, and subsequently to ground or to the power supply 46. Power supply 46, for example, may be a direct current power supply, an alternating current power supply, or a power supply switchable between a direct current and an alternating current. A positive terminal of a direct current power supply, as shown in FIG. 1, may be coupled to the proximal portion of the delivery wire 44 and a negative terminal of a direct current power supply may be coupled to the proximal portion of the handle 42. Power supply 46 may provide a current through the treatment system 10 to initiate an electrolytic process during use of the assembly in a fluid medium such as a bloodstream, which may be used as an electrolyte. A power supply, such as an alternating or direct current power supply, may additionally be used to initiate an electrothrombosis process.

Figure 2:
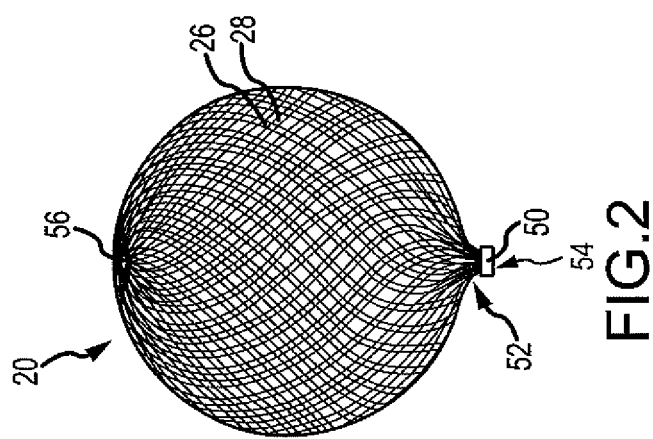
FIG. 2 shows a perspective side view of a braid ball, in accordance with one or more embodiments of the present disclosure.

According to some embodiments, as shown in FIGS. 2 and 3, an implant 20 delivered by the system 10 can be a braid ball. The braid ball 20 can be formed from tubular braid stock including a resilient material, such as Nitinol, that defines an open volume (generally round, spherical, ovular, heart-shaped, etc.) in an uncompressed/unconstrained state. The size of the implant can be selected to fill an aneurysm 2, so the proximal end 52 of the device helps direct blood flow along the surface of the braid from which it is constructed to the branch vessels 8. A distal end 56 of the ball can be dome-shaped. The braid ball 20 can include a single layer or two layers 26, 28 (inner and outer layer, respectively) construction at least where impacted by flow at the neck 9 of the aneurysm 2. As shown, one or more turns of a coil (e.g., Pt wire) or a band (not shown) can provide a distal radiopaque feature to mark the location of the implant 20. Some exemplary implants that can be used in conjunction with the systems described herein are disclosed at U.S. Pub. No. 2013/0123830, published on May 16, 2013, the entirety of which is incorporated herein by reference.

According to some embodiments, the implant 20 can include a hub 50 at a proximal end 52 thereof. The hub 50 can be fixedly attached to the remainder of the implant 20. For example, the hub 50 can grasp braided filaments of the layers 26, 28 of the implant 20. The hub 50 can provide an aperture 54 for receiving engagement and release mechanisms of a delivery system.

According to some embodiments, the implant 20 can be set within an aneurysm sac 2 at a vascular bifurcation 4, formed by trunk vessel 6 and efferent vessels 8. The implant 20 can be delivered by access through the trunk vessel 6 (e.g., the basilar artery), preferably through a commercially available microcatheter with a delivery system as detailed below. To deliver the implant 20, the pusher sleeve 12 is positioned such that the implant 20 can be delivered at least partially into the aneurysm sac 2. After final positioning is achieved as shown in FIG. 3, engagement members are released from the implant 20 (e.g., from a hub 50 of the implant 20), as discussed further herein. Finally, the pusher sleeve 12 is withdrawn into the delivery catheter 48.

While the implant 20 can be a braid ball as illustrated herein, the implant 20 can have any other form or structure, according to various embodiments. For example, the implant 20 can be a vasoocclusive coil, a cylindrical, tube-like stent, or a filter. Other types of implants are generally known. The subject technology can be applied to any such implant for delivery and detachment thereof. For example, a given implant can include a hub 50 for engagement and release by a delivery system, as disclosed further herein.

Figure 5:
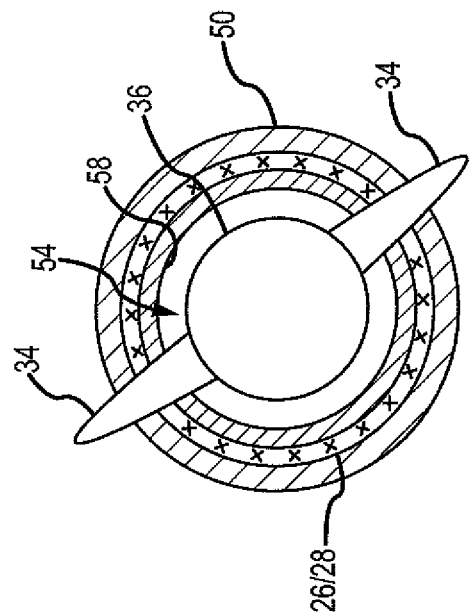
FIG. 5 shows an end view from within the implant of the system shown in FIG. 4, in accordance with one or more embodiments of the present disclosure.
Figure 4:
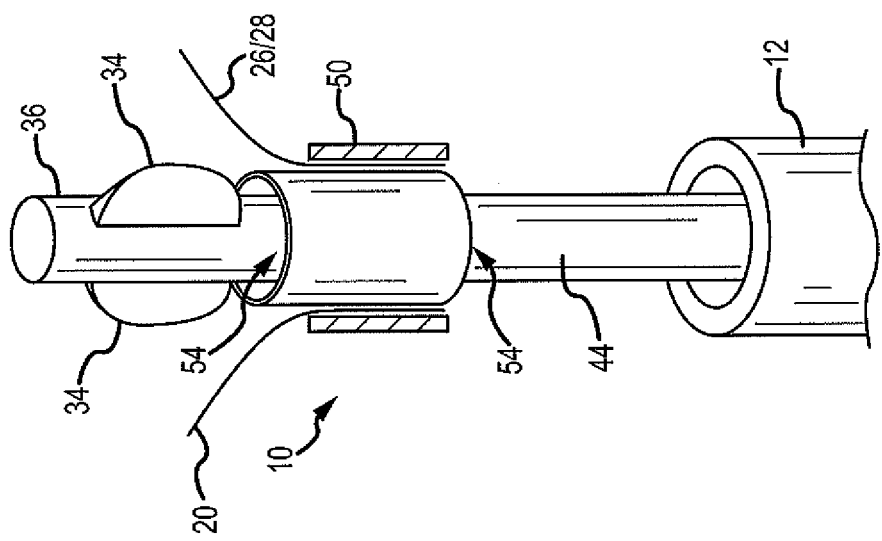
FIG. 4 shows a partial side-sectional view of a distal end of a delivery system, in accordance with one or more embodiments of the present disclosure.

An exemplary detachable delivery system 10 is illustrated in FIGS. 4 and 5. According to some embodiments, one or more flanges 34 are provided to extend radially outward from a core member 36 of the delivery wire 44 to form a stopper. The core member 36 and the flanges 34 may be of the same material or different materials. For example, the flanges 34 may have greater susceptibility to electrolytic corrosion than the core member 36.

According to some embodiments, the delivery wire 44 extends through the aperture 54 of the hub 50, and the core member 36 and the flanges 34 are located distal to the hub 50 of the implant 20. In an engagement state, the flanges 34 extend radially outward to form an outer cross-sectional dimension extending from one radially outward end of one flange 34 to a radially outward end of another flange 34 or the core member 36. In the engagement state, the outer cross-sectional dimension is greater than an inner cross-sectional dimension of an inner surface 58 of the hub 50.

Accordingly, the core member 36 and the flanges 34 cannot pass proximally from a distal side of the hub 50 to a proximal side of the hub 50 while in the engagement state. According to some embodiments, the delivery wire 44 may be provided with tension, such that the hub 50 is held against the pusher sleeve 12 by the flanges 34. According to some embodiments, the delivery wire 44 extends to provide the hub 50 with a range of free motion between the pusher sleeve 12 and the flanges 34.

According to some embodiments, one, more than one, or all of the flanges 34 are electrolytically corrodible. In a corroded (including partially corroded) state, the outer cross sectional dimension defined by the flanges 34 and or the core member 36 is not greater than the inner cross-sectional dimension of the inner surface 58 of the hub 50. Accordingly, the core member 36 and/or any remaining portion of the flanges 34 can pass proximally from a distal side of the hub 50 to a proximal side of the hub 50 while in the corroded state.

Figure 6A:
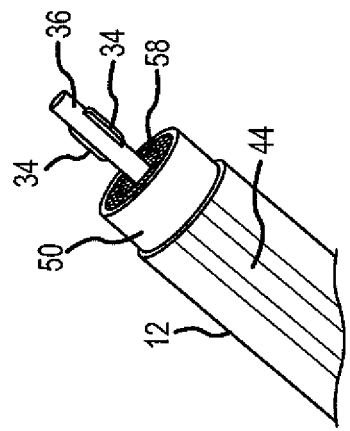
FIGS. 6A, 6B, 6C, and 6D, show partial perspective views of implant detachment with a system, in accordance with one or more embodiments of the present disclosure.
Figure 6B:
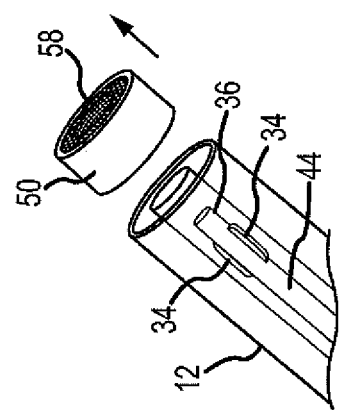
Figure 6C:
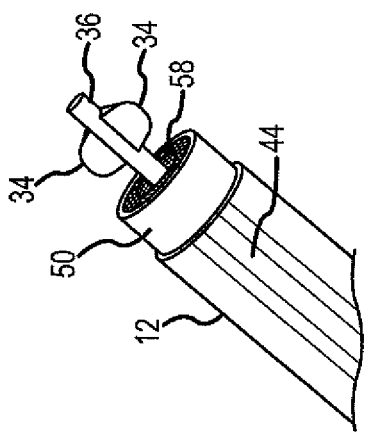
Figure 6D:
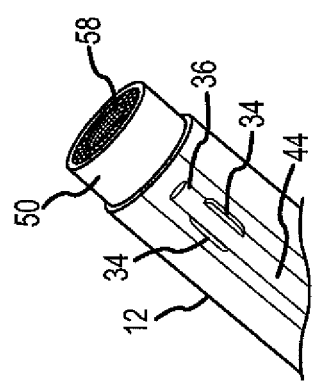

FIGS. 6A-6D illustrate operation of the delivery system 10 in use. The distal end of the detachment system is shown with the hub 50 of an implant 20. FIG. 6A shows the pusher 12 interlock engaged. FIG. 6B illustrates corrosion of the flanges 34 to transition the delivery wire 44 from the engagement state to the corroded state. Upon reducing the outer cross-sectional dimension of the flanges 34 to be less than the inner cross-sectional dimension of the inner surface 58 of the hub 50, the delivery wire 44 can be withdrawn as shown in FIG. 6C. The delivery wire 44 can be withdrawn into the pusher sleeve 12 or along with the pusher sleeve 12. Complete implant (e.g., hub 50) separation is illustrated in FIG. 6D.

According to some embodiments, one or more flanges 34 may be provided in one or more of a variety of shapes, sizes, locations, and orientations. According to some embodiments, one or more flanges 34 may be formed by stamping a generally cylindrical wire to have a flattened section. As shown in FIGS. 7A-B, a stopper can include a single flange 34 that extends radially from a side of the core member 36. An outer cross-sectional dimension can be defined by a radially outward and of the flange 34 and an opposite end of the core member 36.

As shown in FIGS. 8A-B, a stopper can include three or more flanges 34, each extending radially from the core member 36. An outer cross-sectional dimension can be defined by any distance across a triangle defined by the radially outward ends of the flanges 34. According to some embodiments, any number of flanges 34 may be provided. For example, 4, 5, 6, 7, 8, 9, 10 or more flanges may be provided extending radially outward from the core member 36. The flanges 34 can be circumferentially distributed about the core member 36 in an equidistant manner (equal circumferential distance between any pair of adjacent flanges 34). Alternatively or in combination, the flanges can be unevenly circumferentially distributed about the core member 36, such that at least two pairs of adjacent flanges 34 are distributed with unequal circumferential distances there between.

As shown in FIGS. 9A-B, a stopper can include a flange 34 that takes the form of a spherical protrusion from the core member 36. An outer cross-sectional dimension can be defined at an equator or another portion of the spherical flange 34. As shown in FIGS. 10A-B, a stopper can include a flange 34 that takes the form of a cylindrical protrusion from the core member 36. An outer cross-sectional dimension can be defined as the distance between one radially outward end of the flange 34 to a radially opposite end of the flange 34.

According to some embodiments, one or more flanges 34 may taper as it extends radially outward from the core member 36. Accordingly, a thin, radially outer portion of each flange 34 would corrode more rapidly than the wider, radially inner portions. According to some embodiments, one or more flanges 34 can have an axial dimension that exceeds a circumferential dimension thereof. According to some embodiments, one or more flanges 34 can have a circumferential dimensioned that exceeds an axial dimension thereof.

According to some embodiments, as shown in FIGS. 11A-C, an implant 20 may include a hub 50 and an engagement portion including one or more of a ball 96, a rod 94, and a stretch-resistant member 98. The engagement portion of the implant 20 can extend into a cavity 90 of a pusher sleeve 92, distal to an end cap 82, such that the implant 20 is retained in close proximity to the pusher sleeve 92. The pusher sleeve 92 includes the end cap 82 that is entirely or partially electrolytically corrodible. The end cap 82 provides a port 84 having, in an engagement state, an inner cross-sectional dimension that is less than an outer cross-sectional dimension of the ball 96. Accordingly, the ball 96 cannot pass distally out of the pusher sleeve 92 while in the engagement state.

According to some embodiments, the engagement portion (e.g., rod 94 and ball 96) can be attached to the stretch-resistant member 98, which attaches to a portion of the implant 20. The implant 20 preferably has the rod 94 engaging the implant 20 in the proximal direction, with the rod 94 including an eyelet 99 engaging a stretch-resistant member 98, as illustrated in FIG. 11A. More preferably, the stretch-resistant member 98 can pass through the eyelet 99 and wrap the eyelet 99 to form a knot and, most preferably, form a hitch knot. As illustrated in FIG. 11A, when engaging the implant 20, the rod 94 is disposed in the port 84 in the end cap 82 and terminates with the ball 96 disposed proximal to the end cap 82 in the cavity 90.

FIGS. 11A-11C illustrate operation of the delivery system 100 in use. The distal end of the pusher sleeve 92 is shown with the hub 50 of an implant 20. FIG. 11A shows the pusher 92 interlock engaged. FIG. 11B illustrates corrosion of the end cap 82 to transition the end cap 82 from the engagement state to the corroded state. Upon enlarging the inner cross-sectional dimension of the port 84 and the end cap 82 to be greater than the outer cross-sectional dimension of the ball 96, the ball 96 can pass distally out of the pusher sleeve 92 while in the corroded state as shown in FIGS. 11B-C. Complete implant (e.g., hub 50) separation is illustrated in FIG. 11C. As shown, tension in the stretch-resistant member 98 may cause the ball 96 to move entirely proximal to the hub 50 and within the implant 20 when released.

Some exemplary features of a delivery system that can be used in conjunction with the systems described herein are disclosed at U.S. Pub. No. 2010/0030200, published on Feb. 4, 2010, the entirety of which is incorporated herein by reference.

According to some embodiments, a flange 34 and/or an end cap 82 can be configured such that the corrodible portion thereof defines a unique surface structure or texture configured to enhance electrolytic corrosion while preserving the structural characteristics thereof. The features pertaining to any flange 34, as discussed herein, can additionally or alternatively apply to the end cap 82.

For example, the cross-sectional profile of the flange 34 can define at least one concavity, valley, recess, and/or indentation formed therein. In accordance with some embodiments, the cross-sectional profile of the flange 34 can define areas of positive curvature, such as one or more peaks, protrusions, and/or convexities, with areas of negative curvature, such as one or more valleys, recesses, concavities, and/or indentations. The one or more peaks, protrusions, and/or convexities and the one or more valleys, recesses, concavities, or indentations can be formed from surface structures such as grooves, channels, pits, threads, elongate troughs, circumferential or annular grooves, slots, apertures, coils, crimped ribbon, slotted ribbon, perforated ribbon, and/or other such structures that are precisely or randomly arranged. The shape of the cross-sectional profile of the connector body can be defined by one or more linear edges, parallel linear edges, intersecting linear edges, continuous curves, and/or combinations thereof.

By providing a surface structure or texture, some embodiments—can thereby provide an increased surface area of the flange 34 in order to enhance the contact area of the component 206, reduce the overall volume of the flange 34, and thereby improve the rate of corrosion. Further, various embodiments can be provided that are configured to provide excellent structural characteristics in order to ensure that the flange 34 is sufficiently robust and durable.

For example, in some embodiments, the component can have a component body comprising at least one structure, such as a trough, valley, recess, concavity, or indentation defining a recess surface area. In accordance with some embodiments, the component can be configured such that the valley, recess, concavity, or indentation can be used in the component without reducing structural characteristics of the component.

Further, the structure of the flange 34 can add recess surface area to the overall surface area of the flange 34, thereby enhancing electrolytic corrosion of the flange 34. Thus, the ratio of surface area to volume of the flange 34 can increase with an increase in overall surface area and a decrease in volume of the component. As discussed herein, the increase in the overall surface area of the flange 34 can be achieved by the incremental addition of surface area of the structure (e.g., the valley, recess, concavity, or indentation) versus the surface area of a surface without such a structure (e.g., a planar surface). The decrease in volume can be achieved by the addition of the void created by the valley, recess, concavity, or indentation.

Additionally, the flange 34 can be fabricated to provide features that will lead to an increased current density in one or more areas of the flange 34. Such features can include, for example, ridges, edges, small radius corners, valleys, troughs, concavities, recesses, indentations, and/or other structures. In some embodiments, the presence of some of these structures on the flange 34 can reduce the local cross sectional area and/or otherwise contribute to the galvanic reaction. Features that increase current density can accelerate the galvanic reaction.

Additionally, according to some embodiments, the electrolytically corrodible flange 34 can be fabricated using a mechanical cold working operation. The cold working of the flange 34 can be performed through operations such as stamping, drawing, squeezing, bending, and/or other processes. The cold working of the flange 34 can enhance the galvanic reaction or corrosion. For example, as discussed herein, the flange 34 can comprise one or more structures or have a cross section that increases the surface area to volume ratio, which can enhance the galvanic reaction, Further, the process of cold working can alter the material properties of the flange 34, which can improve the anodic quality or corrodibility of the flange 34. Cold working can induce stresses in the material of the flange 34, which can be released during the galvanic reaction, thus facilitating the galvanic reaction. Thus, fabrication of the flange 34 through a cold working operation can further enhance the galvanic reaction.

Furthermore, in accordance with some embodiments, the body of flange 34 can comprise a hollow portion that extends at least partially along the length of the body of flange 34. The hollow portion can be formed as a discrete bubble or as an internal tubular vacuity extending within the body of flange 34. In accordance with some embodiments, the tubular vacuity can extend longitudinally within the body of flange 34. The hollow portion can define one or more sections that are exposed or open to an exterior of the connector body. Accordingly, in such embodiments, the rate of corrosion can be enhanced. Further, it is possible to thereby provide one or more areas where corrosion can be accelerated significantly as the corrosion process reaches the hollow portion(s) of the body of flange 34. As such, one or more hollow portions can be present at one or more sections or points along the body of flange 34.

Accordingly, in some embodiments, the presence of the surface structure(s) on the flange 34 can provide an increased ratio of surface area to volume, compared to a flange 34 that does not have such a structure. Thus, with a higher ratio of surface area to volume, the galvanic reaction can be faster, more predictable, and more effective for some embodiments.

Further, in some embodiments, the presence of a surface feature(s) on the flange 34 can provide increased current density at such feature(s), compared to a flange 34 that does not have such a feature(s). With a higher current density, the galvanic reaction can be faster, more predictable, and more effective for some embodiments.

Other features and discussion of electrolytically corrodible connections is provided in other applications of the present assignee, including the discussion and disclosure of Patent Application Publication No. 2012/0010648 and U.S. Pat. Nos. 7,323,000, and 8,048,104, the entirety of each of which is incorporated herein by reference.

The electrolytically corrodible flange 34 can comprise one or more of the following materials: ceramic materials, plastics, base metals or alloys thereof, and preferably stainless steel. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the medical device can be electrically conductive.

Electrolytically non-corrodible sections of the delivery wire 44 (e.g., the core member 36) can contain one or more of the following materials: noble metals or noble metal alloys, corrosion-resistant ceramic materials, corrosion-resistant plastics, and preferably platinum metal alloys.

According to some embodiments, portions of the delivery wire 44 (e.g., core member 36) can be coated with a nonconductive material. An insulating layer can be provided over at least a portion of an outer surface of the delivery wire 44. For example, the insulating layer can circumferentially surround an outer surface of the delivery wire 44 along a length proximal and/or distal to the flanges 34. An insulating layer can be provided over at least a portion of an outer surface near flanges 34 or circumferentially between flanges. The insulating layer(s) can be of an electrically nonconductive or insulative polymer, such as polyimide, polypropylene, polyolefins, combinations thereof, and the like.

According to some embodiments, the insulating layer(s) leave exposed the flanges 34. When in contact with a body fluid, such as blood, the fluid serves as an electrolyte allowing current to be focused on the non-coated flanges 34. The insulating layer(s) prevent exposure of the delivery wire 44 to the fluid. Accordingly, electrical energy conducted along the delivery wire 44 is concentrated at the flanges 34, thereby reducing the time required to erode away the flanges 34. The insulating layers can be over-molded, co-extruded, sprayed on, or dip-coated with respect to the delivery wire 44.

The use of the above mentioned materials for the formation of electrolytically non-corrodible sections and of the electrolytically corrodible flanges ensures specific electrolytic corrosion of the flanges at the predetermined points.

In accordance with some embodiments, the electrolytically corrodible flange 34 can also be pre-corroded by etching or other methods. Thus, the structure(s) of a given cross-sectional profile can be modified to reduce the presence of corners, increase the recess depth, and/or otherwise enhance the corrosion rate. Further, various excellent structural designs can be provided to achieve desired corrosion performance through the teachings disclosed herein without pre-corrosion of the corrodible points.

Some embodiments can include a corrodible flange 34 that has a partial coating of a material to provide a greater or lesser electrochemical resistance. Thus, in embodiments that have one or more corrodible points, the electrochemical resistance of the points can be varied to achieve staged or preferential electrochemical resistance. Coatings of Zn, Sn, or alloys of such metals on fittings of stainless steel have been found to be particularly satisfactory. Further, some embodiments, the end of the delivery wire can be insulated, for example, by a material coating with reduced corrosion properties or a shrunk-on sleeve to improve its electrochemical resistance.

Embodiments disclosed herein can be used in veterinary or human medicine and more particularly, for the endovascular treatment of intracranial aneurysms and acquired or innate arteriovenous blood vessel deformities and/or fistulas and/or for the embolization of tumors by thrombozation.

The apparatus and methods discussed herein are not limited to the deployment and use of an occluding device within any particular vessels, but can include any number of different types of vessels. For example, in some aspects, vessels can include arteries or veins. In some aspects, the vessels can be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the stent delivery systems disclosed herein can be deployed within super thoracic vessels. The suprathoracic vessels can comprise at least one of intracranial vessels, cerebral arteries, and/or any branches thereof. In some aspects, the stent delivery systems disclosed herein can be deployed within intrathoracic vessels. The intrathoracic vessels can comprise the aorta or branches thereof. In some aspects, the stent delivery systems disclosed herein can be deployed within subthoracic vessels. In some aspects, the stent delivery systems disclosed herein can be deployed within lateral thoracic vessels.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

The invention claimed is:

1. A method, comprising:
    delivering an implant to a target location while (i) a core member of a delivery wire extends through an aperture defined by a hub of the implant and (ii) a stopper of the delivery wire is positioned distal to the aperture and prevents release of the implant from the delivery wire by a first cross-sectional dimension of the stopper, the first cross sectional dimension being greater than an aperture cross-sectional dimension, wherein the stopper and the core member are, together, axially moveable with respect to the hub;
    electrolytically corroding the stopper to reduce the first cross-sectional dimension to a second cross-sectional dimension smaller than the aperture cross-sectional dimension; and
    releasing the implant from the delivery wire by moving the delivery wire entirely proximally past the aperture.

2. The method of claim 1, wherein delivering the implant comprises engaging the hub of the implant with a pusher fixed to the core member at a location proximal to the hub.

3. The method of claim 1, wherein delivering the implant comprises advancing the implant out of a catheter and into a body lumen of a patient.

4. The method of claim 1, wherein electrolytically corroding the stopper comprises inducing an electrical current through the core member and the stopper.

5. The method of claim 1, wherein the core member is formed of a first material and the stopper is formed of a second material more susceptible to electrolytic corrosion than the first material.

6. The method of claim 1, wherein the stopper comprises a flange extending radially outwardly from the core member.

7. The method of claim 6, wherein the flange has a maximum radial dimension smaller than a core member cross-sectional dimension of the core member.

8. A method comprising:
    delivering an implant to a target location while (i) a core member of a delivery wire extends through an aperture defined by a hub of the implant and (ii) a stopper of the delivery wire is positioned completely distally to the hub and prevents release of the implant from the delivery wire by a first cross-sectional dimension of the stopper, the first cross-sectional dimension being greater than an aperture cross-sectional dimension;
    electrolytically corroding the stopper to reduce the first cross-sectional dimension to a second cross-sectional dimension smaller than the aperture cross-sectional dimension; and
    releasing the implant from the delivery wire by moving the delivery wire entirely proximally past the aperture.

9. A method, comprising:
    delivering an implant to a target location while (i) a core member extends through an aperture defined by the implant and (ii) a stopper coupled to the core member is positioned distal to the aperture, the stopper having a first cross-sectional dimension greater than an aperture cross-sectional dimension, wherein the stopper and the core member are, together, axially moveable with respect to the aperture;
    reducing the first cross-sectional dimension of the stopper; and
    releasing the implant from the core member by moving the core member entirely proximally past the aperture.

10. The method of claim 9, wherein the target location is within or adjacent an aneurysm.

11. The method of claim 9, wherein the aperture is defined by a hub of the implant.

12. The method of claim 9, wherein delivering the implant comprises advancing the implant out of a catheter into a body lumen of a patient.

13. The method of claim 9, wherein reducing the first cross-sectional dimension of the stopper comprises electrolytically corroding the stopper.

14. The method of claim 13, wherein electrolytically corroding the stopper comprises inducing an electrical current through the core member and the stopper.

15. The method of claim 13, wherein the core member is formed of a first material and the stopper is formed of a second material more susceptible to electrolytic corrosion than the first material.

16. The method of claim 9, wherein the stopper comprises a flange extending radially outwardly from the core member.

17. The method of claim 16, wherein the flange has a maximum radial dimension smaller than a core member cross-sectional dimension of the core member.

18. The method of claim 9, wherein, before releasing the implant, the stopper is positioned completely distally to the aperture.

* * * * *

UNITED STATES PATENT AND TRADEMARK OFFICE
CERTIFICATE OF CORRECTION

| | |
|---|---|
| PATENT NO. | : 11,839,380 B2 |
| APPLICATION NO. | : 16/948570 |
| DATED | : December 12, 2023 |
| INVENTOR(S) | : Madhur Kadam |

It is certified that error appears in the above-identified patent and that said Letters Patent is hereby corrected as shown below:

In the Claims

In Column 13, in Claim 1, Line 47, delete "cross sectional" and insert -- cross-sectional --, therefor.

Signed and Sealed this
Thirtieth Day of January, 2024

Katherine Kelly Vidal
*Director of the United States Patent and Trademark Office*